(12) United States Patent
Mizobuchi et al.

(10) Patent No.: US 10,052,428 B2
(45) Date of Patent: Aug. 21, 2018

(54) METHODS AND SYSTEMS FOR THE FILTERLESS REDUCTION OF LEUKOCYTES IN A BIOLOGICAL FLUID

(71) Applicant: Fenwal, Inc., Lake Zurich, IL (US)

(72) Inventors: Yoshikazu Mizobuchi, Mundelein, IL (US); Bruce Perry, Akron, OH (US)

(73) Assignee: FENWAL, INC., Lake Zurich, IL (US)

( * ) Notice: Subject to any disclaimer, the term of this patent is extended or adjusted under 35 U.S.C. 154(b) by 273 days.

(21) Appl. No.: 13/838,992

(22) Filed: Mar. 15, 2013

(65) Prior Publication Data

US 2014/0263070 A1 Sep. 18, 2014

(51) Int. Cl.
*A61M 1/36* (2006.01)

(52) U.S. Cl.
CPC ........ *A61M 1/3618* (2014.02); *A61M 1/3679* (2013.01); *A61M 2202/0439* (2013.01)

(58) Field of Classification Search
CPC .............. A61M 1/3618; A61M 1/3679; A61M 2202/0439
USPC ................................................. 210/223, 665
See application file for complete search history.

(56) References Cited

U.S. PATENT DOCUMENTS

| | | | |
|---|---|---|---|
| 5,143,982 A | 9/1992 | Ninno | |
| 5,223,398 A * | 6/1993 | Kortright | G01N 33/5094 435/29 |
| 5,407,581 A | 4/1995 | Onodera et al. | |
| 6,503,761 B1 * | 1/2003 | Koenig | A61K 8/19 252/62.53 |
| 7,057,007 B2 | 6/2006 | Nakamoto et al. | |
| 7,173,124 B2 | 2/2007 | Deggerdal et al. | |
| 7,541,184 B2 | 6/2009 | Berenson et al. | |
| 7,985,340 B2 | 7/2011 | Almaasbak et al. | |
| 2002/0058030 A1 * | 5/2002 | Monroy | A61M 1/3633 424/140.1 |
| 2003/0147883 A1 * | 8/2003 | Wang | C07K 7/06 435/69.1 |
| 2004/0138644 A1 * | 7/2004 | DiCarlo | A61M 25/0043 604/524 |
| 2010/0184069 A1 * | 7/2010 | Fernando | C12Q 1/6806 435/6.12 |
| 2011/0306070 A1 * | 12/2011 | Campbell et al. | 435/7.93 |

OTHER PUBLICATIONS

Product literature entitled M-Beads Magnetic Silica Beads Tools dated 2010 from MoBiTec GmbH.
Product literature entitled M-Beads Magnetic Silica Beads DNA Allround dated 2012 from MoBitec GmbH.
Product literature entitled M-Beads Magnetic Silica Beads DNA dated 2012 from MoBitec GmbH.

* cited by examiner

*Primary Examiner* — Dirk Bass
(74) *Attorney, Agent, or Firm* — Cook Alex Ltd.

(57) ABSTRACT

Methods and systems for removing leukocytes from a biological fluid are disclosed. The methods and systems include a device that has a magnetic substrate coated with one or more polymeric materials that have an adhesion or adsorption affinity for leukocytes.

13 Claims, 3 Drawing Sheets

CONDITIONS: BLOOD/VOLUME PER RUN: 24 HOURS HELD WHOLE BLOOD AT ROOM T°/3 ML
MIXED TIME: 1 HOUR
LEUKOREDUCTION OVER 1 HOUR USING VARYING AMOUNTS OF POLYMER A/MAGNETIC BEADS

CONDITIONS: 24 HOURS HELD WHOLE BLOOD AT ROOM T
WEIGHT RATIO OF COATED POLYMER A/MAGNETIC PARTICLES 0.21 GRAMS/6.1 GRAMS
MIX RATIO OF POLYMER COATED MAGNETIC PARTICLES/BLOOD 0.5 GRAMS/1.5 ML
MIXED TIME: UP TO 360 MINUTES
LEUKOREDUCTION OVER TIME USING 1 GRAM OF POLYMER A/MAGNETIC BEADS PER 3 ML BLOOD

METHODS AND SYSTEMS FOR THE FILTERLESS REDUCTION OF LEUKOCYTES IN A BIOLOGICAL FLUID

FIELD OF THE DISCLOSURE

The present disclosure is directed to methods and systems for reducing the amount of leukocytes in a biological fluid. More particularly, the present disclosure is directed to methods and systems for reducing the amount of leukocytes in a biological fluid without the use of a filter.

BACKGROUND

Before transfusing blood or a collected blood component to a recipient in need of the component, it is often desirable to minimize the presence of impurities or other materials that may cause undesired side effects in the recipient. For example, because of the potential of possible adverse reactions in the recipient, it is generally considered desirable to reduce the number of leukocytes in blood components before transfusion. Reduction in the concentration of leukocytes is often referred to as "leukoreduction".

Filters are widely used to accomplish leukoreduction in blood products today. Filters typically include a filter media disposed between mating walls of a filter housing. Inlet and outlet ports associated with the housing provide flow to and from the interior of the filter. While filters are widely accepted in the field of blood collection and processing, and have generally worked satisfactorily, they are not without certain drawbacks. Passage through a filter often adds time to a blood processing procedure. Also, to ensure proper flow through the filter, there exists the need to monitor the vertical position of the container that holds the blood product being processed as well as the filter. Also, filter performance may vary between filter lots, thus adding to the unpredictability of the time required for a blood processing procedure and the uncertainty of the effectiveness of the leukocyte removal.

Thus, it would be desirable to provide a system and method that allows for more predictability in the time required to leukoreduce a blood product, eliminates the need to monitor the position of the blood source container and the flow-through filter and provides for lot to lot repeatability of the leukoreduction process.

SUMMARY

In one aspect, the present disclosure is directed to a method for removing leukocytes from a biological fluid. The method includes introducing a quantity of a biological fluid including leukocytes and other components into a biocompatible chamber. The biological fluid is contacted inside said chamber with one or more removal devices including a magnetic substrate that is at least partially coated with one or more polymeric materials. The method may also include the step of agitating the chamber. The method further includes applying a magnetic field from a magnetic source that is external to said chamber but in the vicinity of the biological fluid to gather the magnetic removal devices in a part of the chamber. The other remaining components may then be removed from the chamber.

In another aspect, the present disclosure is directed to a system for reducing the number of leukocytes in a biological fluid. The system includes a container having an interior chamber, a device that includes a magnetic substrate at least partially coated with one more polymeric materials and at least one magnet external to said container. The system may further include a flow path in openable fluid communication with the chamber.

In a more specific aspect, the device may be or include a plurality of particles having a magnetic substrate that is coated with one or more polymeric materials. The polymeric materials may be selected to enhance the adhesion or adsorption of leukocytes.

DETAILED DESCRIPTION OF THE EMBODIMENTS

Figure 1:
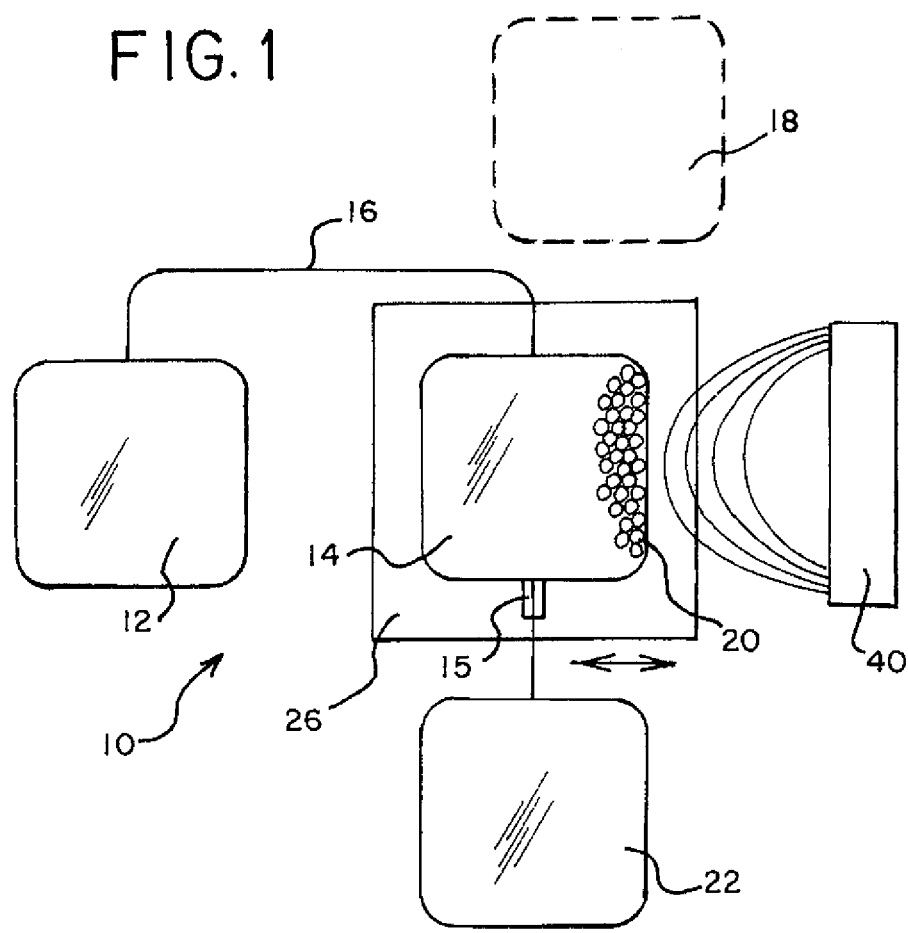
FIG. 1 is a schematic view of a system in accordance with the present disclosure.

The present disclosure is directed to systems and methods for reducing the number leukocytes in a biological fluid. As shown in FIG. 1, the system 10 may include a source of biological fluid 12 and a mixing chamber 14 where the biological fluid is combined and contacted with one or more removal devices that effect the reduction and removal of leukocytes from the biological fluid. Source 12 may be in flow communication with mixing chamber 14. Flow communication between source 12 and mixing chamber 14 may be provided by tubing 16 which defines an openable flow path between container 12 and chamber 14. System 10 may also include a source of removal devices 18. Removal devices 20 may be separately introduced into mixing chamber 14 before, during or after introduction of the biological fluid into chamber 14. Alternatively, removal devices 20 may be provided in mixing chamber 14 at the time of manufacture. Where the removal devices include a magnetic substrate, system 10 may further include one or more magnets 40 for generating a magnetic field and gathering or otherwise attracting the removal devices to a particular location of the chamber 14. System 10 may also optionally include a collection container 22 for collecting the unbound components from chamber 14, if desired.

In accordance with one aspect of the present disclosure, the source of biological fluid 12 may be a blood donor. In another preferred embodiment, the source 12 may be a container of biological fluid that has been previously collected from a donor.

The biological fluid may be any biological fluid that includes leukocytes. In one example, the biological fluid may be whole blood. In another embodiment, the biological fluid may be a component of blood. Where the source of biological fluid 12 is previously collected blood, container 12 that holds the biological fluid may be made of a medical-grade polymeric material such as, but not limited to, plasticized polyvinyl chloride.

Mixing chamber 14 may be any receptacle that is suitable for holding blood, components of blood or any other biological fluid. In one embodiment, mixing chamber 14 may be a sealed container made of a polymeric material. To effect and/or enhance mixing, system 10 may preferably include a mixing device 26 such as a mixer or shaker on which chamber 14 may be mounted and rotated, tilted or otherwise agitated to enhance contact of the biological fluid and the removal device(s) 18.

Figure 2:
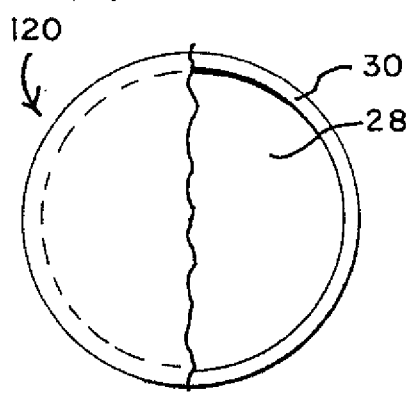
FIG. 2 is a perspective view with a portion cut-away of an exemplary removal device in the form of a particle.
Figure 3:
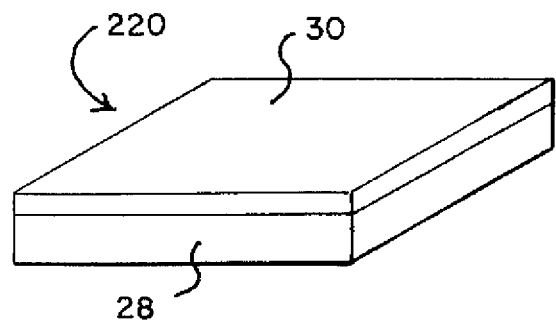
FIG. 3 is a perspective view of an alternative embodiment of a removal device.

In accordance with the present disclosure, system 10 includes one or more such removal devices 18. In one embodiment, removal device 18 includes a substrate 28 and a coating 30 on the substrate as seen in FIGS. 2 and 3. The coating is preferably a material that allows for adhesion or adsorption of leukocytes on the device surface. The substrate is preferably a magnetic substrate and the coating is preferably a polymeric material that, as indicated above, allows for adhesion or adsorption of leukocytes on the device surface.

In a preferred embodiment, the removal device may be a particle or a bead having a magnetic substrate and a polymeric coating. Magnetic particles or other affinity beads are well known and are available from a variety of sources. Suitable particles and beads and the manufacturers of such particles and beads suitable for use in the methods and systems of the present disclosure include Dynabeads available from Invitrogen, M-beads from Pharmacia, Luminex magnetic beads from Millipore and magnetic beads from Lake Industries, Inc. of Saint Marys, Ga.

In one non-limiting example, magnetic particles or beads may be generally spherical particles 120 as shown in FIG. 2 having a diameter of approximately 1 µm-1 mm and, more preferably approximately 1 µm-100 µm. In an alternative embodiment, shown in FIG. 3, the removal device 20 may be provided as a plate having a magnetic substrate and a polymeric coating. The magnetic substrate 28 of plate 220 may have a thickness of approximately 0.1 µm-1 mm and more preferably, approximately 0.1 µm-100 µm and a width of approximately 0.1 µm-1 mm and more preferably, approximately 1 µm-100 µm.

Whether the magnetic substrate of the removal device 20 disclosed herein is a bead/particle or a plate, the magnetic substrate is covered with a polymeric coating 30. The polymeric coating may be a single polymeric compound or a blend of polymeric compounds. The polymers selected or at least one of the polymers selected allow for adhesion or adsorption of leukocytes with its surface. In one embodiment, coating 30 may be made of one or more of the following polymeric compounds: polyethylene terephthalate, polybutylene terephthalate, polyethylene, polypropylene, polyvinyl chloride including plasticized polyvinyl chloride and non-plasticized polyvinyl chloride, and polystyrene. Polymeric coating 30 may be applied as a layer having a thickness of approximately 1 nm to approximately 1 mm and more preferably approximately 1 µm to approximately 100 µm.

In accordance with the method of reducing leukocytes in a biological fluid as disclosed herein, a quantity of a biological fluid such as whole blood or a blood component that has been separated from whole blood that includes leukocytes and other components is introduced from a source 12 such as a container or directly from a patient into biocompatible mixing chamber 14. The biological fluid is contacted with one or more removal devices comprising a magnetic substrate that is at least partially coated with one or more polymeric materials inside said chamber. Where the removal device is a polymeric coated magnetic particle or bead of the type described above, a plurality of beads may be introduced from a source container 18 that holds beads 20. Alternatively, mixing chamber 14 may be provided with beads 20. The biological fluid remains in contact with the removal device for a selected period time. To enhance contact between the biological fluid and the removal device, such as beads 20, mixing chamber 14 may be agitated for a period of time. In one embodiment, mixing chamber may be agitated for anywhere between approximately 5 and 15 minutes, preferably at room temperature. Leukocytes are adhered to or adsorbed by the polymeric material on the outer surface of the particle or bead 20 or other removal device. After sufficient mixing, one or more magnetic fields provided by one or more magnetic devices 40 external to chamber 14 but in the vicinity of mixing chamber is/are applied. The magnetic field causes the particles or beads to accumulate or gather at a wall of mixing chamber 14. The other remaining components which have now had their leukocyte content reduced may then be removed from the chamber, by for example flowing the remainder of the biological fluid out port 15 of mixing chamber 14 into a collection container 22. The collected, leukoreduced biological fluid may be stored and/or transfused to a recipient or patient.

Leukoreduction in accordance with the methods and systems disclosed herein eliminates the need for a leukocyte reduction filter. The methods and systems disclosed herein also allow the leukoreduction to be tailored to specific needs or targets such as the percentage of the leukocytes to be reduced or the targeting of certain leukocytes such as lymphocytes or neutrophils for reduction. These specific needs and targets may be achieved by selecting a specific particle size distribution, by selecting a specific ratio of particles and biological fluid, by selecting specific polymers for specific needs or combining two or more polymers to achieve a desired separation and/or by combining two more particulates (particles or beads) each coated with a different polymer coating.

STUDY

Figure 4:
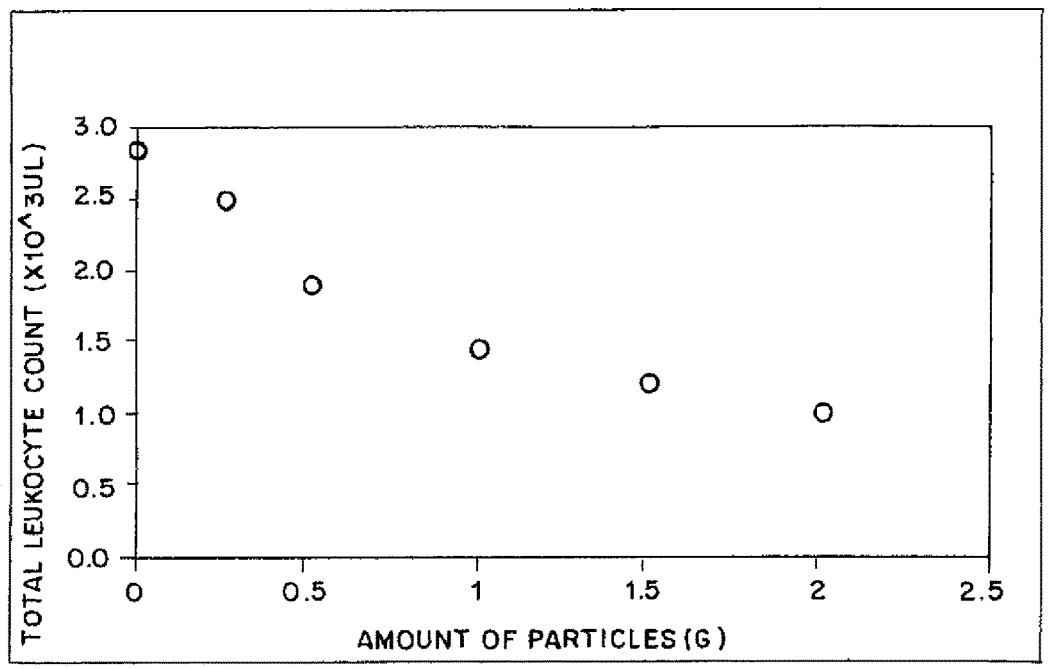
FIG. 4 is a graph showing the level of leukocyte removal for different amounts of polymer-coated magnetic particles.
Figure 5:
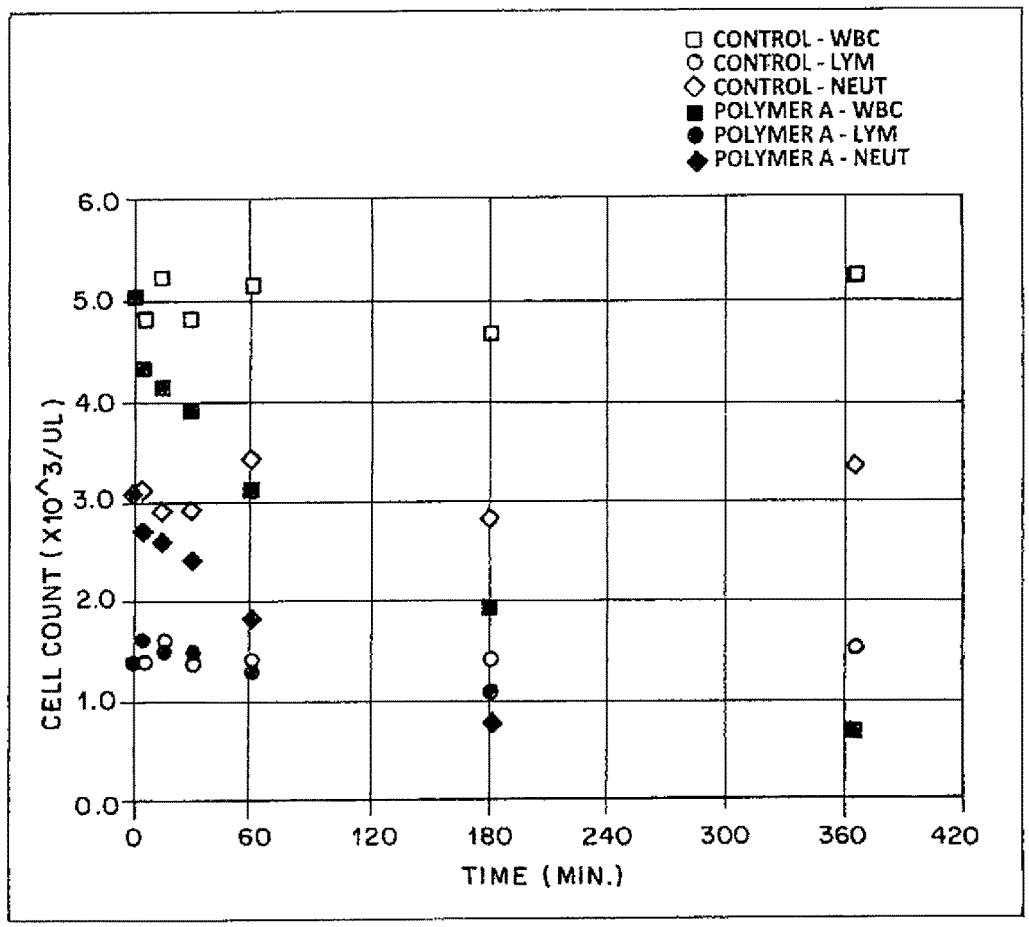
FIG. 5 is a graph showing the levels of leukoreduction over time using polymer-coated magnetic particles of the present disclosure.

Several different polymers were used to prepare beads in accordance with the present disclosure. The polymers included polyvinyl chloride, polystyrene and a polymer that includes plasticized polyvinyl chloride referred to herein as Polymer A. Each of the polymers was dissolved in approximately 10 ml of tetrahydrofuran and hand mixed with magnetic particles. The magnetic particles were particles 3000-4 (particle sizes ranging between 1 µm to 20 µm) and particles 3000-15 (average particle size 0.7 µm), both obtained from Lake Industries, Inc. of Saint Marys, Ga. The mixture was air-dried in a hood overnight at room temperature. A typical weight of the polymer to the magnetic bead (approximately 6-7 grams) was approximately 0.2 grams. The polymer coated magnetic particles were combined with blood products (MNC product, or fresh whole blood or blood that had been held for 24 hours at room temperature) in 20 ml capped plastic cups and spun on a vortex mixer for approximately 1 hour. The ratio of particles to blood in the mixture was approximately 1 g particles/3 ml blood. Controls with no beads and uncoated beads were also used and analyzed. The blood products were analyzed for leukocounts using a Sysmex counter. The results are shown in Table 1 below and in FIGS. 4 and 5. In Table 1, the cell count units for WBC (White Blood Cells), Lym (Lymphocytes), Mxd (Mxd=WBC (Lym+Neut), Neut (Neutrophils) and PLT (Platelets) are expressed in $1\times10^3/\mu L$. Thus, for example, the WBC cell count after a 24 hour hold with no treatment is $14.1\times10^3/\mu L$.

TABLE 1

| Description | 24 Hr. Hold, No Treatment | Control, No Beads | Uncoated Mag. | Uncoated Mag. | Polymer A + Mag. | Polymer A + Mag. |
| --- | --- | --- | --- | --- | --- | --- |
| Magnetic Type | — | — | 3000-4 | 3000-4 | 3000-4 | 3000-4 |
| Amount (g) of Coating Per 7 g of Magnetite | — | — | — | — | 0.2 | 0.2 |
| Grinding | — | — | — | — | Hand | Hand |
| WBC | 14.1 | 13.0 | 10.3 | 11.3 | 6.2 | 6.4 |
| Lym Mxd Neut | 11.9 | 11.1 | 9.7 | 10.6 | 6.0 | 6.2 |
| PLT | 223 | 225 | 165 | 155 | 165 | 141 |
| % Change WBC | — | −10 | −29 | −22 | −57 | −56 |
| % Change Lym % Change Mxd % Change Neut | — | −7 | −18 | −11 | −50 | −48 |
| % Change PLT | — | 6 | −23 | −27 | −23 | −34 |

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

The invention claimed is:

1. A method for separating and collecting a transfusible blood product including red blood cells with a substantially reduced population of leukocytes of a specific type from a blood product source comprising:
   Introducing from said source a quantity of said blood product including red blood cells and leukocytes of said specific type and other components into a biocompatible chamber, said chamber comprising a sealed container made of a polymeric substance;
   Contacting inside said chamber said blood product with a plurality of particles, each of said particles comprising a magnetic substrate coated with one more polymeric materials selected from the group of polyethylene terephthalate, polybutylene terephthalate, polyethylene, polypropylene, polyvinyl chloride selected to allow for adhesion or adsorption of said leukocytes of a specific type to said one or more polymeric materials;
   Agitating said blood product with said particles;
   Attaching said leukocytes to said coated particles by adhesion or adsorption;
   Applying a magnetic field external to said chamber in the vicinity of said biological fluid blood product to aggregate said attached leukocytes in a portion of said chamber;
   Separating said red blood cells from said leukocytes within said chamber;
   Removing said red blood cells from said chamber; and
   Transfusing said red blood cells to a subject.

2. The method of claim 1 wherein said coating with one or more polymeric materials has a thickness of approximately 1 nm to approximately 1 mm.

3. The method of claim 1 wherein said coating with one or more polymeric materials has a thickness of approximately 1 μm to approximately 100 μm.

4. The method of claim 1 comprising contacting said blood product with a plurality particles coated with a first polymeric coating selected to effect adhesion or adsorption of a first type of leukocyte to said first polymeric coating and a plurality of particles coated with a second and different polymeric coating selected to effect adhesion or adsorption of a second type of leukocyte to said second and different polymeric coating.

5. The method of claim 1 wherein said source of said blood product comprises whole blood.

6. The method of claim 1 wherein said source of said blood product comprises red blood cells previously separated from whole blood.

7. The method of claim 1 wherein the weight ratio of said coating with one or more polymeric materials to magnetic substrate in one of said particles is approximately 0.21/6.2 grams.

8. The method of claim 1 wherein said mixture ratio of particles to said blood product from said source comprises approximately 0.5 grams/1.5 ml.

9. The method of claim 4 comprising agitating said blood product source with said at least one or more devices at room T°.

10. The method of claim 1 wherein said leukocytes of a specific type are neutrophils.

11. The method of claim 1 wherein said leukocytes of a specific type are lymphocytes.

12. The method of claim 1 wherein said coating with one or more polymeric materials comprises polyvinyl chloride.

13. The method of claim 12 wherein said polyvinyl chloride is plasticized.

* * * * *